United States Patent
Perreault (10) Patent No.: US 9,983,189 B2
(45) Date of Patent: May 29, 2018

(54) DETECTION OF OIL CONTAMINATION IN ENGINE AIR

(71) Applicant: PRATT & WHITNEY CANADA CORP., Longueuil (CA)

(72) Inventor: Jean-François Perreault, Hemmingford (CA)

(73) Assignee: PRATT & WHITNEY CANADA CORP., Longueuil, QC (CA)

( * ) Notice: Subject to any disclaimer, the term of this patent is extended or adjusted under 35 U.S.C. 154(b) by 281 days.

(21) Appl. No.: 15/055,102

(22) Filed: Feb. 26, 2016

(65) Prior Publication Data

US 2017/0248571 A1 Aug. 31, 2017

(51) Int. Cl.
*G01N 33/28* (2006.01)
*F02C 3/00* (2006.01)

(52) U.S. Cl.
CPC .......... *G01N 33/2888* (2013.01); *F02C 3/00* (2013.01); *F05D 2220/32* (2013.01); *F05D 2240/55* (2013.01); *F05D 2260/80* (2013.01); *F05D 2270/803* (2013.01)

(58) Field of Classification Search
CPC ... G01N 33/2888; F02C 3/00; F05D 2220/32; F05D 2240/55; F05D 2260/80; F05D 2270/803; G01M 15/14; B64F 5/40; B64F 5/60

See application file for complete search history.

(56) References Cited

U.S. PATENT DOCUMENTS

| | | | | |
|---|---|---|---|---|
| 4,732,861 A * | 3/1988 | Sinclair | ................. | G01N 25/30 436/159 |
| 4,755,360 A * | 7/1988 | Dickey | ................. | B01D 53/86 422/122 |
| 5,750,999 A | 5/1998 | Fox | | |
| 6,067,865 A * | 5/2000 | Molter | ............... | G01N 15/0205 73/865.5 |
| 6,957,569 B1 | 10/2005 | Napier et al. | | |
| 7,089,747 B2 * | 8/2006 | Fox | ......................... | G01N 1/22 60/782 |
| 7,122,065 B2 * | 10/2006 | Fox | ......................... | G01N 1/24 55/306 |
| 7,159,475 B2 * | 1/2007 | Casillas | ................... | G01N 1/22 73/864.34 |
| 7,250,141 B2 * | 7/2007 | Collins | ............. | B01D 53/8675 422/177 |
| 8,938,973 B2 | 1/2015 | Dooley et al. | | |
| 9,020,764 B2 * | 4/2015 | Walte | ................. | G01N 33/0032 250/281 |
| 9,776,725 B2 * | 10/2017 | Fox | ........................ | B64D 13/06 |
| 2005/0188773 A1 | 9/2005 | Fox et al. | | |

(Continued)

FOREIGN PATENT DOCUMENTS

EP 1701160 A1 * 9/2006 ............ B64D 13/00

*Primary Examiner* — David Bolduc
(74) *Attorney, Agent, or Firm* — Norton Rose Fulbright Canada LLP (57) ABSTRACT

There is described an oil contamination detection system and method. The system comprises a forward sensor package, a rearward sensor package, a catalytic chamber, and a computing device. The method comprises obtaining sensor measurements from the forward sensor package and the rearward sensor package, and detecting the presence of oil in the air flow from the sensor measurements.

20 Claims, 6 Drawing Sheets

(56) References Cited

U.S. PATENT DOCUMENTS

| | | | |
|---|---|---|---|
| 2005/0229686 A1* | 10/2005 | Napier | G01M 3/025 73/112.01 |
| 2007/0086008 A1* | 4/2007 | Schweighardt | G01N 15/06 356/337 |
| 2008/0302672 A1* | 12/2008 | Sandvik | G01N 33/2841 205/775 |
| 2010/0206042 A1* | 8/2010 | Johns | F01N 11/00 73/23.31 |
| 2011/0192170 A1* | 8/2011 | Dooley | B64D 13/02 60/785 |
| 2013/0030718 A1 | 1/2013 | Williams et al. | |
| 2014/0157872 A1* | 6/2014 | Welland | G01N 15/0656 73/28.02 |
| 2015/0020529 A1* | 1/2015 | Hoskin | F02C 3/30 60/772 |
| 2015/0049786 A1* | 2/2015 | Wang | G01M 15/14 374/138 |
| 2015/0308293 A1* | 10/2015 | Huntington | F02C 3/34 60/772 |
| 2017/0184472 A1* | 6/2017 | Fechner | G01N 33/0004 |
| 2017/0211468 A1* | 7/2017 | Devarakonda | F02B 73/00 |

\* cited by examiner

DETECTION OF OIL CONTAMINATION IN ENGINE AIR

The application relates generally to aircraft engines and, more particularly, to sensing oil contamination in air samples from the engine.

BACKGROUND OF THE ART

Oil contamination in aircraft cabin air is undesirable. Typically, pressurized air provided to aircraft cabins is bled from an engine aboard the aircraft. However, the bled air can become contaminated with oil. Even a small amount of oil contamination is detectable by people in the aircraft cabin. One source of oil contamination is worn carbon seals used in aircraft engines. As the seals deteriorate, the risk of bleed air contamination increases as small amounts of oil may leak past the seal. In order to avoid contamination incidents, carbon seals are replaced often, and perhaps earlier than may actually be necessary. However, this is not a very cost effective way to optimize the use of carbon seals. Room for improvement exists.

SUMMARY

There is described an oil contamination detection system and method. The system comprises a forward sensor package, a rearward sensor package, a catalytic chamber, and a computing device. The method comprises obtaining sensor measurements from the forward sensor package and the rearward sensor package, and detecting the presence of oil in the air flow from the sensor measurements.

In one aspect, there is provided an oil contamination detection system for an aircraft engine, the engine having a compressor and an oil system. The detection system comprises a forward sensor package mountable to the engine upstream of the compressor and comprising a first set of sensors for obtaining baseline measurements from ambient air; a catalytic chamber having a catalytic surface therein for causing a catalytic reaction, the catalytic chamber in fluid communication with an outlet of the compressor; a rearward sensor package mountable to the engine downstream from the compressor, the rearward sensor package having a second set of sensors configured for obtaining pre-chamber measurements from engine compressor outlet air upstream of the catalytic chamber, and a third set of sensors configured for obtaining post-chamber measurements from the reacted engine compressor outlet air downstream of the catalytic chamber; and a computing device comprising a processor and a memory coupled to the forward sensor package and the rearward sensor package, and configured for receiving measurement data comprising the baseline measurements, the pre-chamber measurements, and the post-chamber measurements and detecting a presence of oil in the air from the measurement data.

In another aspect, there is provided an engine with the oil contamination detection system mounted thereto.

In yet another aspect, there is provided a method for detecting oil contamination in an air flow bled from an aircraft engine, the engine having a compressor and an oil system. The method comprises obtaining baseline measurements from a first sample of air at a first set of sensors mounted to an engine upstream from the compressor; obtaining pre-chamber measurements from a second sample of air at a second set of sensors mounted to the engine downstream from the compressor; circulating the second sample of air through a catalytic chamber having a catalytic surface for causing a catalytic reaction; obtaining post-chamber measurements from the second sample of air from a third set of sensors mounted to the engine downstream from the catalytic chamber; and detecting a presence of oil in the air flow from measurement data comprising the baseline measurements, the pre-chamber measurements, and the post-chamber measurements.

DESCRIPTION OF THE DRAWINGS

Reference is now made to the accompanying figures in which.

DETAILED DESCRIPTION

Figure 1:
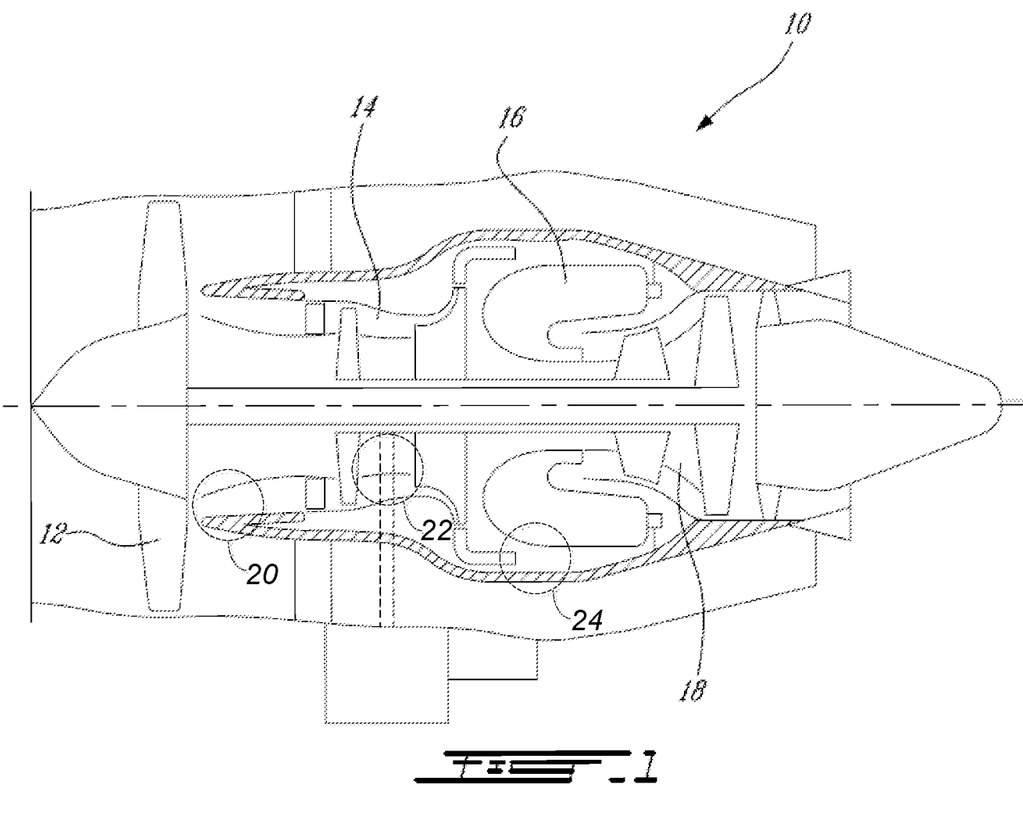
FIG. 1 is a schematic side cross-sectional view of an exemplary gas turbine engine.

FIG. 1 illustrates an exemplary engine 10, namely a gas turbine engine, comprising an inlet 12, through which ambient air is propelled, a compressor section 14 for pressurizing the air, a combustor 16 in which the compressed air is mixed with fuel and ignited for generating an annular stream of hot combustion gases, and a turbine section 18 for extracting energy from the combustion gases. Engine seals may be found throughout the engine 10, such as in a gearbox or along a main shaft. An oil contamination detection system may be mounted directly to the engine 10 in order to sample engine air and detect a present of oil. The system may also be used to evaluate engine seal wear condition for seals that aerosolize oil.

While the engine 10 is shown to be a turbofan engine, the oil contamination detection system and method described herein may also be used for other types of gas turbine engines, such as turbo shaft and turbo prop engines. The system is also applicable to other types of internal combustion engines, such as jet engines, as well as any other engine type having seals therein for preventing leakage of oil from the engine. As the detection system may be mounted to the engine 10 while the engine operates, it's weight should be minimized. In some embodiments, the system is less than 2 kg. In some embodiments, the system is powered from an alternator of the engine 10.

Air is sampled from at least two areas of the engine 10. The first area is upstream from the compressor 14, such as at an engine air intake location 20. Ambient air may be sampled from the engine air intake location 20. The second area is downstream from the compressor 14, for sampling compressed air, at locations such as post-compressor location 22 or pre-combustor location 24. In an engine design having a first stage compressor and a second stage compressor, the second area may be after the first stage compressor or after the second stage compressor.

Figure 2:
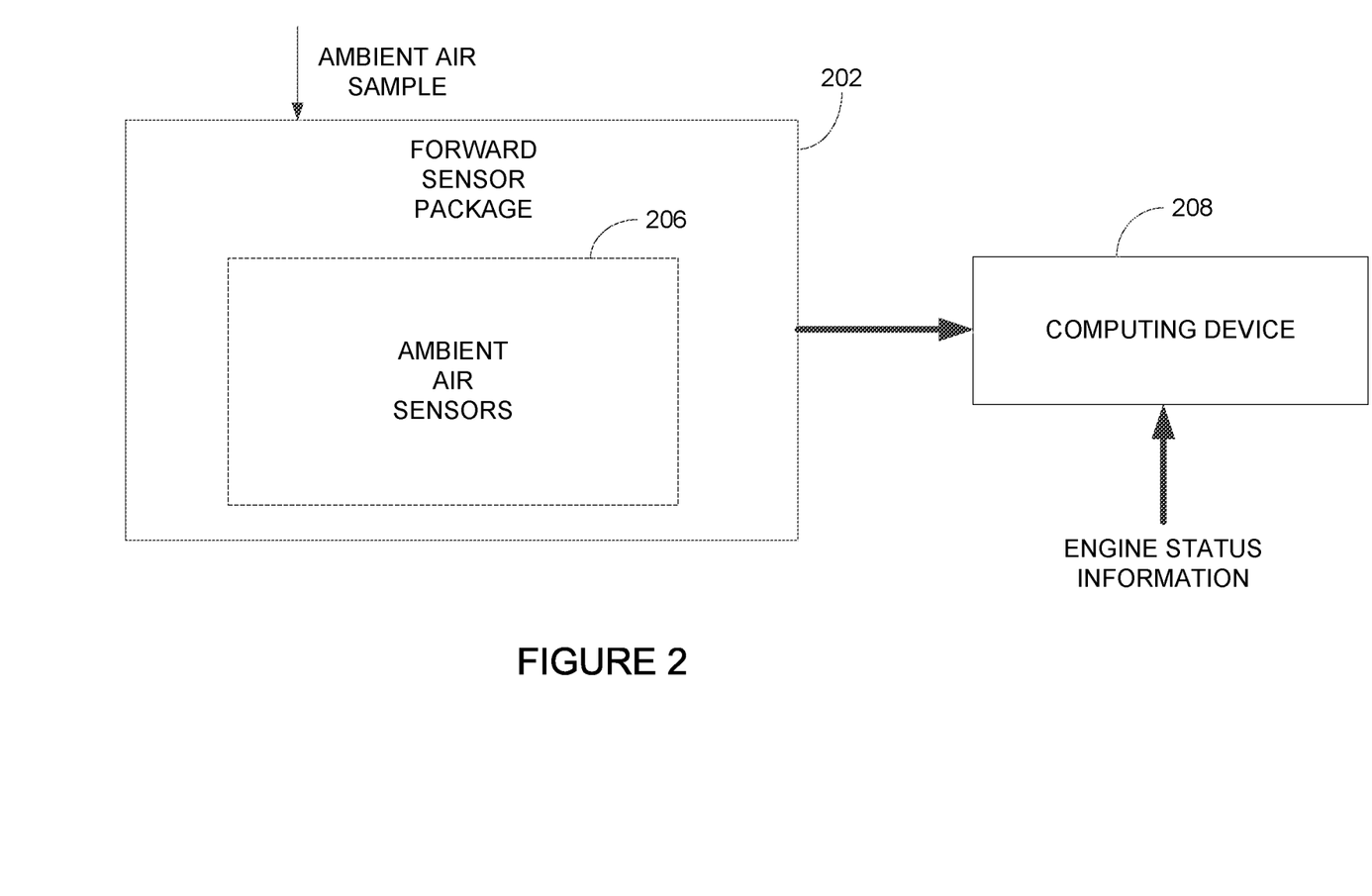
FIG. 2 is a block diagram of an embodiment of a first portion of an oil contamination detection system.

Referring to FIG. 2, there is illustrated an example embodiment for a forward sensor package 202, mountable at an engine air intake such as at location 20, and used to sample the ambient air. The forward sensor package 202 comprises a plurality of ambient air sensors 206 which are arranged to obtain baseline measurements from the ambient air. In some embodiments, the ambient air sensors 206 comprise a plurality of different sensor types. For example, there may be one or more of any one of a humidity and air temperature sensor, an optical particle count sensor, a carbon dioxide sensor, a wideband oxygen sensor, and an air pressure sensor, and an air flow mass sensor. The humidity and air temperature sensor provides on-condition calibration data. The wideband oxygen sensor establishes a baseline for the amount of unreacted oxygen in the air. Similarly, the optical particle count sensor and the carbon dioxide sensor establish a baseline for particle count and carbon dioxide, respectively. The air pressure sensor and the air flow mass sensor may be used to calibrate the output values of other sensors, as well as help coordinate other parts of the system, such as a heating element controller and a valve controller. Collected sensor measurements are transmitted to a computing device 208. Note that for all of the figures representing block diagrams, data signal flow is illustrated with thicker lines and air flow is illustrated with thinner lines.

Figure 3:
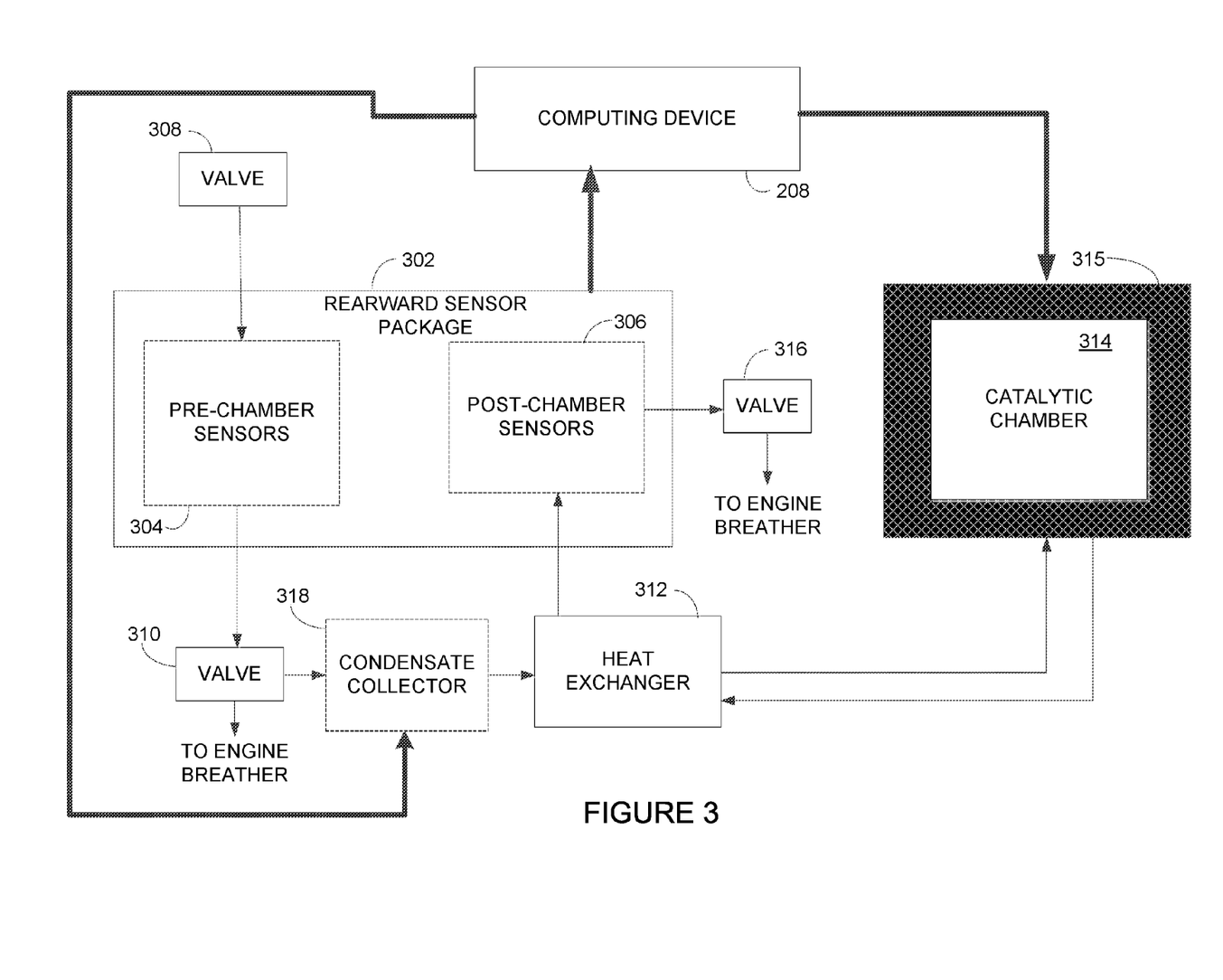
FIG. 3 is a block diagram of an embodiment of a second portion of the oil contamination detection system.

Referring to FIG. 3, there is illustrated an example embodiment for a rearward sensor package 302, used to sample the compressed air, and mountable to the engine downstream from the compressor, such as at location 22 or 24. In some embodiments, the rearward sensor package 302 is mounted to a blow-off valve of the engine found at either location 22 or 24. The rearward sensor package comprises two separate sets of sensors, namely pre-chamber sensors 304 and post-chamber sensors 306. The pre-chamber sensors 304 are arranged to sample the compressed air as received from the compressor section 14, such as via a valve 308, which may be a needle valve or another type of valve. Pre-chamber measurements are obtained by the pre-chamber sensors 304. Once sampled, the compressed air is circulated through a catalytic chamber 314. Catalyzed air is then provided to the post-chamber sensors 306, for obtaining post-chamber measurements therefrom. The pre-chamber measurements and post-chamber measurements are then provided to the computing device 208.

The catalytic chamber 314 is arranged to be in fluid communication with an outlet of the compressor. In some embodiments, the flow of air between the catalytic chamber 314 and the rearward sensor package 302 is effected by a heat exchanger 312. In some embodiments, the heat exchanger 312 also pre-heats air received from the pre-chamber sensors before providing it to the catalytic chamber 314. This may be done, for example, to reduce energy needed to heat the air in the catalytic chamber 314.

In some embodiments, the flow of air between the pre-chamber sensors 304 and the heat exchanger 312 occurs via a valve 310. In some embodiments, valve 310 is a two-way valve that can selectively send the flow of air from the pre-chamber sensors 304 to the heat exchanger 312 or to an engine breather. Compressor air may thus be diverted to the engine breather without passing through the heat exchanger 314, for example when the chamber is not heated. This may be done, for example, to reduce power consumption when the engine seal maintenance system is inactive and to avoid polluting the catalytic chamber 314.

The catalytic chamber 314 serves to oxidize hydrocarbons found in the compressor air. It may take various forms, such as cylindrical, rectangular, square, and other shapes, including irregular shapes. An insulation layer 315 may encase the chamber 314, so as to prevent heat loss therefrom. The insulation layer may be composed of materials having a high melting point, such as glass wool, refractory ceramic fibres, and polycrystalline wool. Other materials may also be used. The insulation layer 315 may be of a given thickness, such as 1 inch, 2 inches, 3 inches, and other suitable values. In some embodiments, the catalytic chamber 314 is a close fitting cylindrical heating element with a built-in thermocouple and high temperature shut-off. In some embodiments, the catalytic chamber 314 is designed to heat air to between 400 and 700 degrees Fahrenheit.

Inside the catalytic chamber 314 is a heating element and a catalytic surface for causing a catalytic reaction. In some embodiments, the catalytic surface is one or more coiled pieces of wire coated with a catalyzing agent, such as palladium, platinum, and other catalysts that have hydrocarbon decomposing properties. Alternatively, the wire itself may be made from a catalytic material. In other embodiments, the catalytic surface is a honeycomb structure either coated with or made from a catalytic material. The structure may be made from ceramic or other materials capable of withstanding the high temperatures of the catalytic chamber 314.

The pre-chamber sensors 304 are arranged to obtain baseline measurements from the compressor air. In some embodiments, the pre-chamber sensors 206 comprise a plurality of different sensor types. For example, there may be one or more of any one of a humidity and air temperature sensor, an air mass flow sensor, an optical particle count sensor, a carbon dioxide sensor, a wideband oxygen sensor, an air pressure sensor, and one or more hydrocarbon sensors. The humidity and air temperature sensor provides baseline humidity and temperature values for the compressor air. The wideband oxygen sensor establishes a baseline for the amount of unreacted oxygen in the compressor air. The optical particle count sensor and the carbon dioxide sensor establish a baseline for particle count and carbon dioxide, respectively, for the compressor air. The air pressure sensor may be used to monitor sensing conditions. The air mass flow sensor may be used to determine a precise amount of air entering the rear sensor package 302 via valve 308. The hydrocarbon sensors may be MQ series gas sensors or other such sensors capable of detecting the presence of hydrocarbons in the compressed air and establish a baseline for hydrocarbons. Pre-chamber measurements are transmitted to the computing device 208.

The post-chamber sensors 306 are arranged to obtain comparative measurements from the compressor air post-catalyzing in the catalytic chamber 314. Therefore, the post-chamber sensors 306 may be the same type of sensors as the pre-chamber sensors 304. One or more of the pre-chamber sensors 304 may be omitted from the post-chamber sensors 306, such as the air mass flow sensor, as there is no need for measurements of air mass flow post-chamber. An air pressure sensor in the post-chamber sensors 306 may be used to detect clogging of the catalytic chamber 314 and/or the heat exchanger 312, and/or to detect a faulty valve, by comparing air pressure before the catalytic chamber 314 and/or the heat exchanger 312 with air pressure after the catalytic chamber 314 and/or the heat exchanger 312. A variation in air pressure may then be indicative of the clogging/faulty valve. Note that clogging can be cleared by opening one or more valves during take-off, and catalyst poisoning can be reversed by closing off chamber valves and setting a heating element in the chamber to a maximum temperature. Post-chamber measurements are transmitted to the computing device 208.

Heated compressor air may exit the rearward sensor package 302 via a valve 316, such as a solenoid valve. Valve 316 may be an on-off switch that blocks off the end of the air path through the rearward sensor package 302 until it is opened. It may be used to seal the system when not in use. In some embodiments, valve 316 and valve 310 are fitted with a one-way valve at their outlet to prevent contaminated breather air from back flowing into the system.

In some embodiments, due to the generally low levels of oil contaminants in the pre-chamber compressor air and/or post-chamber compressor air, a condensate collector 318 can be used to concentrate the oil contaminants to a minimum detectable level. The condensate collector 318 is a fluid receptacle, such as a tank or pan, over which is placed a coiled tube or other gas-to-gas heat exchanger. The flow of air between the pre-chamber sensors 304 and the heat exchanger 312 passing through the valve 310 may be passed through the condensate collector 318, though the valve 310 may also bypass the condensate collector 318. The minimum detectable level may be determined by the nature of the oil contaminants, by the type of sensors in the rearward sensor package 302, by the operating conditions of the rearward sensor package 302, such as temperature, and the like. Therefore, the minimum detectable level is variable.

Operation of the condensate collector 318 may be controlled by the computing device 208. A thermocouple (not illustrated) may be placed at an output port of the condensate collector 318 to provide the computing device 208 with temperature readings from the condensate collector 318. The condensate collector 318 may only be operable under certain conditions, such as when the ambient air is below a predetermined condensation threshold (such as −50 C, for example), and during certain portions of flight, such as during a cruise portion of the flight.

When the conditions are met, the computing device 208 activates the condensate collector 318. Valve 310 is connected to a selector valve (not illustrated), and a portion of the air passing through valve 310 is diverted by the selector valve to the coiled tube of the condensate collector 318. The diverted air is circulated through the coiled tube, and the remaining air is sent to the heat exchanger 312 through the condensate collector 318, but not through the coiled tube, causing condensation of any organic residue in the remaining air. The organic residue condensate then collects in the fluid receptacle. The computing device 208 can also adjust the output from valve 310 to the selector valve to control the temperature of the diverted air circulated through the coiled tube.

After a set amount of time, or if the fluid receptacle becomes clogged by ice crystals, or if the operating conditions of the condensate collector 318 are no longer met, or based on any other suitable factor, the computing device 208 activates a heater (not illustrated) of the condensate collector 318. The valve 310 is set by the computing device 208 to route all air through the condensate collector 318 to the heat exchanger 312, but not through the coiled tube. The computing device 208 may monitor the temperature of the air to ensure that the air passing through the condensate collector 318 does not exceed a threshold temperature, such as 150 C, to prevent hydrocarbon decomposition. The air passed through the condensate collector 318 can pick up the organic residue condensate collected in the fluid receptacle, which is then measured by the post-chamber sensors 306.

In some cases, a second coiled tube (not illustrated) of the condensate collector 318 is added to make a three-way gas-gas-liquid heat exchanger. The first coiled tube is configured for routing the diverted air from the selector valve, and the second coiled tube is configured for routing a low-boiling-point refrigerant solution. The second coiled tube is connected to a powered vapor compression low temperature refrigeration unit (not illustrated) to lower the temperature of the refrigerant solution. The addition of the second coiled tube may allow for more generous operating conditions, such as increased sensitivity at lower altitudes and at higher ambient air temperatures.

Figure 4:
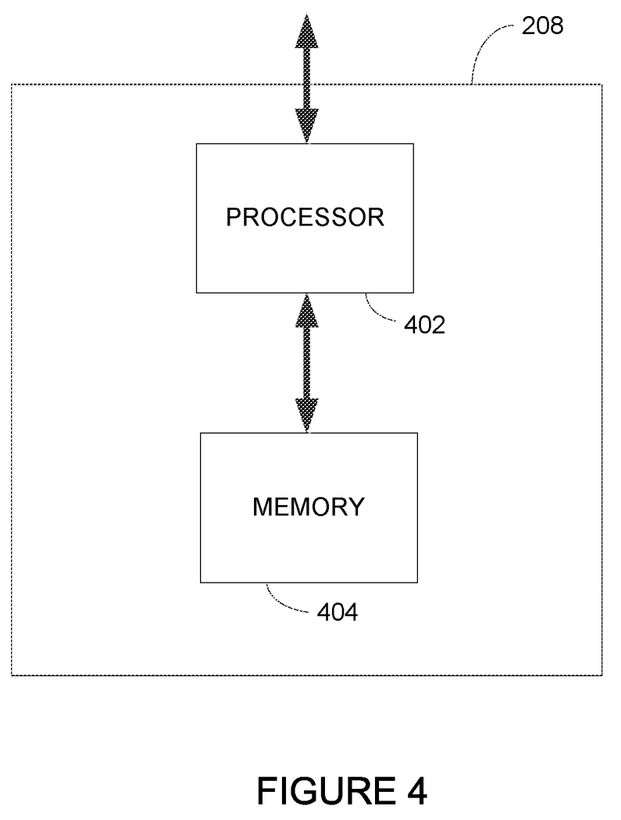
FIG. 4 is a block diagram of an embodiment of a computing device from the oil contamination detection system.

An example embodiment of the computing device 208 is illustrated in FIG. 4. The computing device 208 may comprise any suitable type of processor 402, for example, any type of general-purpose microprocessor or microcontroller, a digital signal processing (DSP) processor, an integrated circuit, a field programmable gate array (FPGA), a reconfigurable processor, a programmable read-only memory (PROM), or any combination thereof. In some embodiments, processor 402 corresponds to a system-on-chip. In some embodiments, the system-on-chip is a 32 bit microcontroller.

Computing device 208 may also comprise any suitable type of memory 404, the memory being located internally or externally. For example, the computing device 208 may include random-access memory (RAM), non-volatile RAM, read-only memory (ROM), optical-disc-based read-only memory, electro-optical memory, magneto-optical memory, erasable programmable read-only memory (EPROM), electrically-erasable programmable read-only memory (EEPROM), Ferroelectric RAM (FRAM), and the like. In some embodiments, memory 404 is composed of multiple types of memories, for example a RAM memory and one or more redundant raw data storage memory card, such as a 64 GB micro Secure Digital (SD) card.

The computing device 208 may comprise an interface (not shown) in order to communicate with other engine and/or aircraft components, to access and connect to other resources, and to perform other computing applications by connecting to one or more other computing devices. The computing device 208 may also comprise other components, such as a multichannel analog to digital converter, a clock, and a power conditioner. In some embodiments, engine status information is provided to the computing device 208 from an engine electronic controller, such as shaft rotation per minute (RPM), power level, oil temperature, etc. This information may be used by the computing device 208 to determine whether the engine is active and to perform sensing and oil presence detection accordingly. For example, the computing device 208 may be configured to operate at certain predetermined engine operation times, such as at take-off of the aircraft.

Operation of the computing device 208 will be described with reference to FIG. 5, which is a flowchart of a method for detecting oil contamination in an air flow bled from an aircraft engine. At step 502, baseline measurements are obtained from the ambient air sensors 206, which are mounted upstream from the compressor. At step 504, pre-chamber measurements are obtained from the pre-chamber sensors 304, which are mounted downstream from the compressor. Steps 502 and 504 may be performed concurrently or sequentially. In some embodiments, step 502 is performed continuously while step 504 is only performed periodically, at predetermined intervals. These intervals may be every 10 minutes, every 20 minutes, every hour, or any other suitable time interval. The time interval may be based on actual time or engine operation time. For example, step 504 may be performed every 10 minutes throughout a day, or it may be performed at every 10 minutes of operation of the engine 10.

Airflow over the pre-chamber sensors 304 may be controlled by the computing device 208 via valve 308. For example, valve 308 may be a needle valve controlled by a screw thread and adjustable with high precision via a small electric motor on request from the processor 402. To assist the processor 402 in selecting the right position for valve 308, a mass airflow sensor from the pre-chamber sensors 304 returns to the processor 402 the exact amount of air entering the system. A thermocouple at the end of the catalytic chamber 314 may be used to determine how hot the air gets. The processor 402 may then control the amount of heat applied and the amount of flow with the goal of maintaining the minimum amount of flow which is still enough to get positive results. Engine and/or atmospheric conditions may have an impact on the required air flow.

At step 506, compressor air is circulated through the catalytic chamber 314, which is positioned downstream from the compressor and is in fluid communication with an outlet of the compressor. The computing device 208 may perform step 506 by controlling the catalytic chamber 314 with regards to its temperature. It may also control the flow of air from the pre-chamber sensors 304 to the catalytic chamber 314 via valve 310.

At step 508, post-chamber sensor measurements are obtained from the post-chamber sensors 306 positioned downstream from the catalytic chamber 314. At step 510, the presence of oil is detected in the air flow from the measurement data.

In some embodiments, step 512 is also performed, either by the computing device 208 or by another similar device to which the measurement data has been provided. In step 512, engine seal wear condition is evaluated as a function of the measurement data. Evaluating engine seal wear condition may comprise comparing the measurement data to one or more predetermined thresholds and determining an engine seal wear condition. For example, the engine seal wear condition may correspond to acceptable, pre-failure, or failure, as a function of the level of oil detected in the air.

In some embodiments, a step 514 of transmitting a signal with the engine seal wear condition may be performed. The signal may be output by the computing device 208 towards an engine computer and/or an aircraft computer. For example, the engine seal wear condition signal may be sent to the FADEC, which may be reprogrammed to read the engine seal wear condition signal. The engine seal wear condition signal may also be sent to an instrument panel in a cockpit, as a warning signal or alert that at least one engine seal needs replacement. The signal may be sent through existing aircraft wiring harness. The signal may be sent independently on the aircraft wiring harness, or it may be overlaid on top of an existing signal, such as a BOV control signal. Alternatively, the signal may be sent wirelessly through one or more networks. In addition to step 514 or in combination therewith, a maintenance flag may be set when the engine seal wear condition is one of pre-failure and failure.

Engine seal wear condition may be determined using a "sensor fusion" technique, whereby data from several different sensors are fused to compute an output that could not be determined by any one sensor alone. Indeed, the levels of oil to be detected in the air flow that are indicative of engine seal wear are particularly low and thus very difficult to obtain with a single sensor.

For example, using carbon dioxide sensors, there should be no increase in carbon dioxide between measurements obtained from the ambient air and measurements obtained from the pre-heat compressor air. If there is, it may be indicative of exhaust gas path leakage into intake path, or of fuel or oil in the intake passages getting decomposed by high pressures and temperatures at an outlet of the compressor 14.

Similarly, an increase in carbon dioxide between the pre-chamber sensors 304 and the post-chamber sensors 306 may be indicative of the presence of organic contaminants in the compressor air and thus, a failure or pre-failure wear level of an engine seal. The hydro carbon sensors may be used to detect oil or fuel residue in the compressor air, pre and post heating. The pre-chamber sensors 304 directly detect the presence of hydrocarbons in the compressor air, and the post-chamber sensors 306 are used to determine an increase or decrease in hydrocarbons after the catalytic reaction. Both an increase and a decrease of hydrocarbons may be indicative of increased oil contaminants and therefore a failure or pre-failure wear level for an engine seal. The levels of hydrocarbons in the pre-catalyzed compressor air may be so low that multiple types of hydrocarbon sensors are required to augment the sensitivity of the sensors. For example, propane sensors, alcohol sensors, and halocarbon sensors can detect different hydrocarbon chain lengths and configurations.

The particle count sensors may be used to detect an increase in dust, soot, silt, fines, and other particles between ambient air, pre-chamber compressor air, and post-chamber compressor air. An increase in particle count relative to engine intake is indicative of an increase in engine bleed air contamination. A bleed air contamination level threshold may be set, below which oil levels may be found acceptable. Two thresholds may be used above the acceptable level, a first one for detecting a pre-failure wear level and a second and higher one for detecting a failure wear level.

An increase in particle count between pre-chamber and post-chamber may also be indicative of a pre-failure and/or failure wear level. The catalytic chamber 314 serves to break down molecules and create lighter hydrocarbons, but it will also create free carbon particles (i.e. soot). This soot may be detected by the particle count sensors when the quantity reaches a certain level. In some embodiments, the air may be passed through progressively finer filters and sensed with a particle count sensor at the output of each filter in order to detect particles of different sizes. For example, a first sensor may be exposed to the raw air, a second sensor may be exposed to air filtered through a 10 micron filter, and a third sensor may be exposed to air filtered through a 1 micron filter. This may help to distinguish more benign particles from more damaging particles as a size threshold may be used as indicative of a leak. The size threshold may vary as a function of oil type, engine operating conditions, such as oil temperature, outlet air temperature, type of seal used and amount of wear of the seal. The filter mesh sizes may vary as a function of the engine operating conditions as well.

The wideband oxygen sensors may be used to measure the amount of unreacted oxygen in the ambient air, pre-chamber compressor air, and post-chamber compressor air. The baseline is set using the ambient air and a subsequent decrease may be indicative of an increase in engine bleed air contamination. Oxygen threshold levels may be set for pre-failure and/or failure wear levels. Humidity sensors may be used to measure humidity levels, whereby an increase in humidity may be indicative of the complete oxidation of hydrocarbon molecules.

Pre-failure and/or failure wear levels may be determined based on a frequency of contamination events and/or an amplitude of events. For example, repeated small peaks on all sensing elements may be indicative of increased seal wear and engine air contamination. In some embodiments, the processor 402 is configured to estimate a time until seal failure based on the sensor measurements and historical data obtained from other engines. For example, historical data may indicate that when a given engine type was at level X, there was Y runtime left until failure. In some embodiments, the processor 402 is configured to identify which seals of the engine 10 are in need of change, if not all seals are at a same wear level.

Any thresholds used by the processor 402 for establishing a wear level may be determined from prior engine monitoring data collected over time. Additional data used for the analysis may also be obtained from an engine computer such as a Full Authority Digital Engine Controller (FADEC) or an Electronic Engine Control (EEC), or from an aircraft computer. The additional data may include engine variables such as engine output torque, engine output power, high-pressure and low-pressure rotor speed, fuel flow rate, oil level sensor reading, engine oil temperature, intake air temperature, calculated intake air flow rate, and exhaust gas temperature. The data may be stored in the memory 404 or in a database provided remotely from the system. Sensor characterization maps may also be stored in the memory 404 for sensor calibration purposes.

Figure 6:
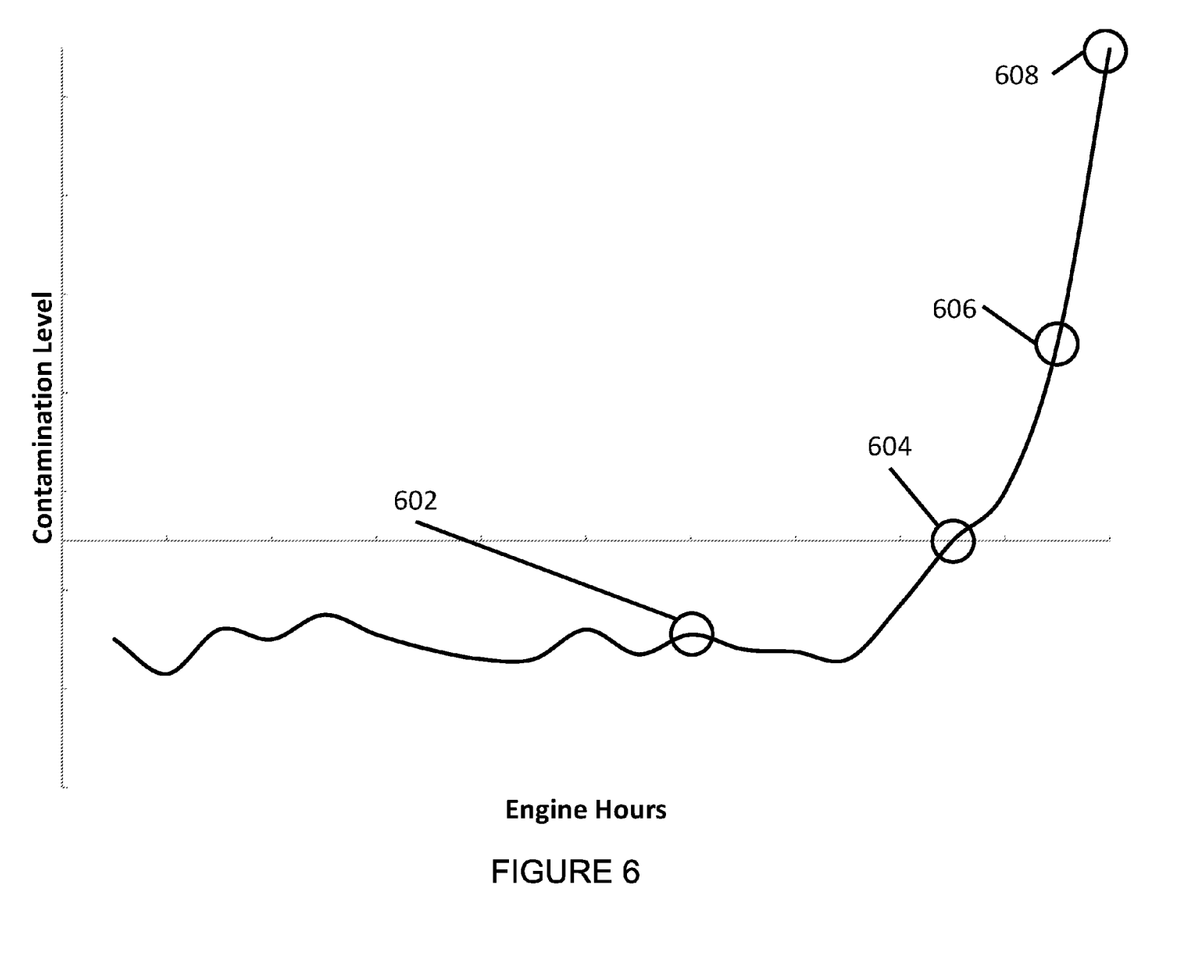
FIG. 6 is a graph of an example curve for engine hours versus contamination level.

With reference to FIG. 6, in some embodiments the processor 402 is configured to track the variance of contamination levels, via particle count, for example, over time in order to determine pre-failure and/or failure wear levels. The aforementioned sensor fusion technique is used to track the contamination level to determine when a particular contamination threshold point 604 is reached. Once the contamination threshold point 604 is reached, the processor 402 indicates, for example to the FADEC and/or the EEC, that the seal has reached a pre-failure wear level requiring replacement of the seal. The processor 402 can also indicate that a failure wear level point 606, such as a smell-in-cabin event, or that a catastrophic failure wear level point 608, such as an engine destruction event, is reached, based on the tracking of the contamination levels. The contamination levels may be tracked for pre-chamber compressor air and/or post-chamber compressor air.

For example, an existing replacement protocol based not on contamination level but on a service lifecycle value, such as a predetermined number of hours of use, takes place at point 602. However, the seal is still serviceable until a contamination threshold point 604, after which point the viability of the seal is exponentially diminished. The processor 402 tracks the contamination levels until the contamination threshold point 604, then indicates that the seal is to be replaced. If the seal is not replaced upon the contamination levels reaching the contamination threshold point 604, the processor 402 continues to track the contamination levels, and indicates that failure and/or catastrophic failure wear levels are about to be reached when the contamination levels approach points 606 and 608, respectively. The contamination threshold point 604, as well as the failure wear level point 606 and the catastrophic failure wear level point 608 may be based on previously-acquired historical contamination level data, or may be derived from theoretical equations. Additionally, while FIG. 6 shows the contamination level as following an exponential "hockey-stick graph", it should be noted that other contamination level patterns are also considered.

In some embodiments, the processor 402 can also track the contamination levels to formulate a "time-to-failure" prediction. For example, the processor 402 can estimate a number of remaining serviceable hours for the seal based on the contamination levels, and predict the number of hours until reaching each of points 604, 606, and 608, or any other point on the graph of FIG. 6. The time-to-failure may also be based on previously-acquired historical contamination level data, and on previous time-to-failure predictions. In particular, the processor 402 can use historical tracking data of a number of service hours required to reach each of points 604, 606, and 608 in other seals and estimate a time-to-failure based on the historical tracking data and the contamination levels. Other factors, such as use environment, disuse time, and the like, may also be considered when the processor 402 formulates a time-to-failure prediction.

Figure 5:
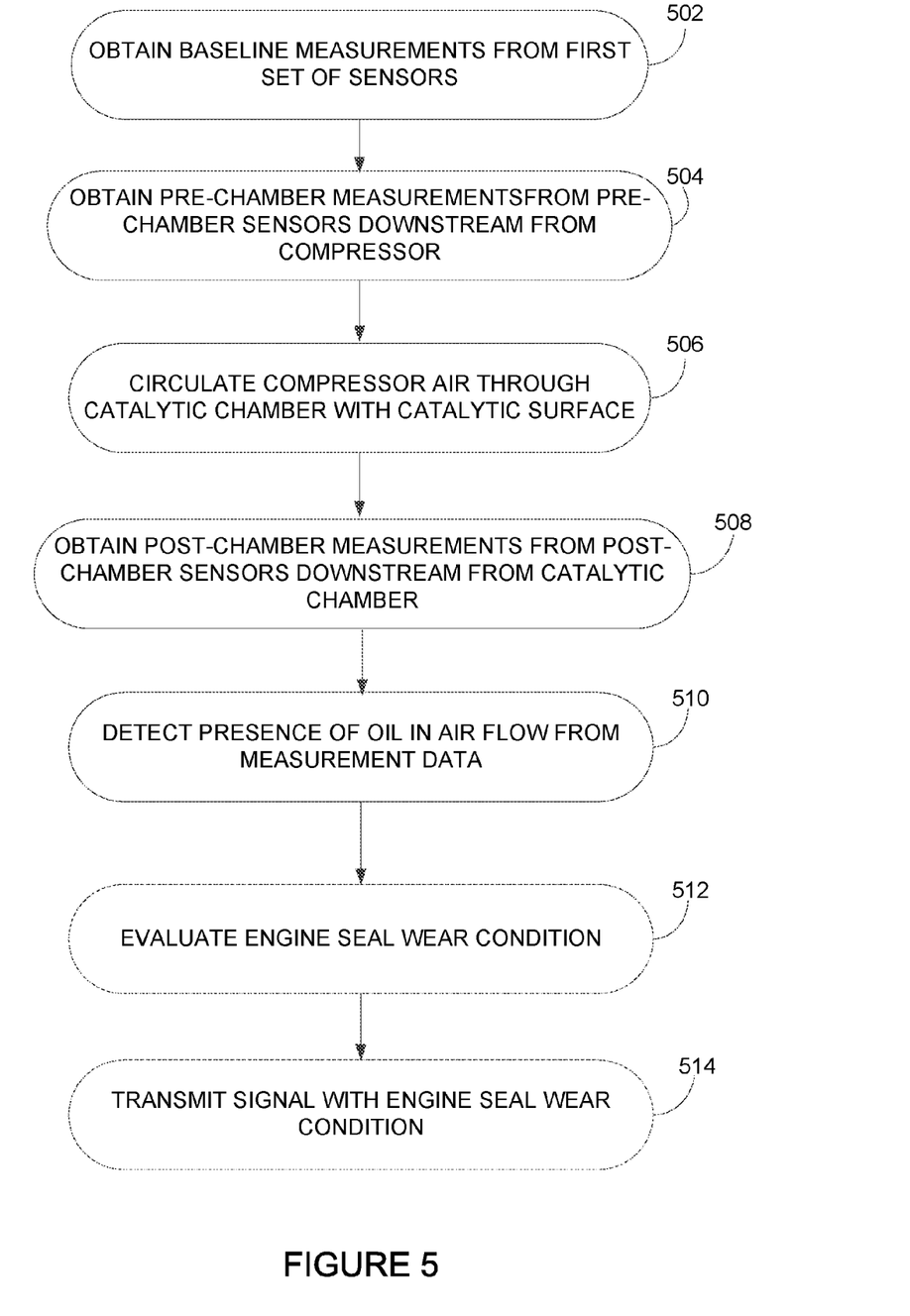
FIG. 5 is a flowchart of an embodiment of a method for oil contamination detection.

Various computer programs may be stored in the memory 404 and run on the processor 402 in order to perform any of the steps described in the method of FIG. 5. The programs may be implemented in a high level procedural or object oriented programming or scripting language, or a combination thereof. Alternatively, the programs may be implemented in assembly or machine language. The language may be a compiled or interpreted language. Embodiments of the system may also be considered to be implemented by way of a non-transitory computer-readable storage medium having one or more computer programs stored thereon. The computer programs may comprise computer-readable instructions which cause the processor 402 to operate in a specific and predefined manner to perform the functions described herein.

Various aspects of the present engine seal wear detection system may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Although particular embodiments have been shown and described, it will be obvious to those skilled in the art that changes and modifications may be made without departing from this invention in its broader aspects. The appended claims are to encompass within their scope all such changes and modifications.

The invention claimed is:

1. An oil contamination detection system for an aircraft engine, the engine having a compressor and an oil system, the detection system comprising:
a forward sensor package mountable to the engine upstream of the compressor and comprising a first set of sensors for obtaining baseline measurements from ambient air;
a catalytic chamber having a catalytic surface therein for causing a catalytic reaction, the catalytic chamber in fluid communication with an outlet of the compressor;
a rearward sensor package mountable to the engine downstream from the compressor, the rearward sensor package having a second set of sensors configured for obtaining pre-chamber measurements from engine compressor outlet air upstream of the catalytic chamber, and a third set of sensors configured for obtaining post-chamber measurements from the reacted engine compressor outlet air downstream of the catalytic chamber; and
a computing device comprising a processor and a memory coupled to the forward sensor package and the rearward sensor package, and configured for receiving measurement data comprising the baseline measurements, the pre-chamber measurements, and the post-chamber measurements and detecting a presence of oil in the air from the measurement data.

2. The system of claim 1, wherein the computing device is further configured for evaluating engine seal wear as a function of the measurement data.

3. The system of claim 2, wherein evaluating engine seal wear comprises comparing the measurement data to at least one predetermined threshold and determining an engine seal wear condition.

4. The system of claim 3, wherein the computing device is further configured for sending a signal with the engine seal wear condition.

5. The system of claim 3, wherein the engine seal wear condition is selected from a group comprising acceptable, pre-failure, and failure.

6. The system of claim 5, wherein the computing device is further configured for setting a maintenance flag when the engine seal wear condition is one of pre-failure and failure.

7. The system of claim 1, wherein:
the first set of sensors comprises a first humidity and air temperature sensor, a first optical particle count sensor, a first carbon dioxide sensor, and a first wideband oxygen sensor;
the second set of sensors comprises a second humidity and air temperature sensor, a second optical particle count sensor, a second carbon dioxide sensor, an air mass flow sensor, a second wideband oxygen sensor, and a first set of hydrocarbon sensors; and
the third set of sensors comprises a third humidity and air temperature sensor, a third optical particle count sensor, a third carbon dioxide sensor, a third wideband oxygen sensor, and a second set of hydrocarbon sensors.

8. The system of claim 1, wherein the rearward sensor package further comprises a heat exchanger arranged between the second set of sensors, the catalytic chamber, and the third set of sensors.

9. The system of claim 1, wherein the computing device is configured for controlling valves of the engine to allow airflow at least one of in and out of the system.

10. An engine comprising the system of claim 1 mounted thereon.

11. A method for detecting oil contamination in an air flow bled from an aircraft engine, the engine having a compressor and an oil system, the method comprising:
obtaining baseline measurements from a first sample of air at a first set of sensors mounted to an engine upstream from the compressor;
obtaining pre-chamber measurements from a second sample of air at a second set of sensors mounted to the engine downstream from the compressor;
circulating the second sample of air through a catalytic chamber having a catalytic surface for causing a catalytic reaction;
obtaining post-chamber measurements from the second sample of air from a third set of sensors mounted to the engine downstream from the catalytic chamber; and
detecting a presence of oil in the air flow from measurement data comprising the baseline measurements, the pre-chamber measurements, and the post-chamber measurements.

12. The method of claim 11, further comprising evaluating engine seal wear as a function of the measurement data.

13. The method of claim 12, wherein evaluating engine seal wear comprises comparing the measurement data to at least one predetermined threshold and determining an engine seal wear condition.

14. The method of claim 13, further comprising transmitting a signal with the engine seal wear condition.

15. The method of claim 13, wherein the engine seal wear condition is selected from a group comprising acceptable, pre-failure, and failure.

16. The method of claim 15, further comprising setting a maintenance flag when the engine seal wear condition is one of pre-failure and failure.

17. The method of claim 11, wherein obtaining baselines measurements, obtaining pre-chamber measurements, and obtaining post-chamber measurements comprises sampling air from the engine at regular intervals during engine operation.

18. The method of claim 11, wherein obtaining baselines measurements, obtaining pre-chamber measurements, and obtaining post-chamber measurements comprises obtaining measurements from at least three different types of sensors in each of the first set of sensors, the second set of sensors, and the third set of sensors.

19. The method of claim 11, further comprising pre-chamber the second sample of air prior to having it heated in the catalytic chamber.

20. The method of claim 11, further comprising selectively opening and closing valves of the engine to receive the second sample of air at the second set of sensors, circulate the second sample of air between the second set of sensors, catalytic chamber, and third set of sensors, and output the second sample of air after obtaining the post-chamber measurements.

* * * * *